United States Patent [19]

Tonne et al.

[11] 4,393,211

[45] Jul. 12, 1983

[54] PREPARATION OF AROMATIC SULFOHALIDES

[75] Inventors: Peter Tonne, Neustadt; Hagen Jaedicke, Ludwigshafen, both of Fed. Rep. of Germany

[73] Assignee: BASF Aktiengesellschaft, Ludwigshafen, Fed. Rep. of Germany

[21] Appl. No.: 320,334

[22] Filed: Nov. 12, 1981

[30] Foreign Application Priority Data

Feb. 28, 1981 [DE] Fed. Rep. of Germany ....... 3107700

[51] Int. Cl.$^3$ .................. C07D 215/36; C07C 143/70
[52] U.S. Cl. ................................. 546/153; 260/543 R; 260/401; 260/402; 260/505 R; 260/505 C; 546/155; 546/157; 546/294; 560/10; 560/12; 560/13; 560/14; 560/139; 560/142; 562/427; 562/429; 562/430
[58] Field of Search ................... 260/543 R, 401, 402, 260/505 R, 505 C; 546/153, 155, 157, 294; 560/10, 12, 13, 14, 139, 142; 562/427, 429, 430

[56] References Cited

U.S. PATENT DOCUMENTS 3,248,423 4/1966 Stratton .......................... 260/543 R
4,097,526 1/1978 Chan ............................... 260/543 R

FOREIGN PATENT DOCUMENTS 859461 12/1952 Fed. Rep. of Germany ... 260/543 R
955682 4/1964 United Kingdom ............ 260/543 R

OTHER PUBLICATIONS

Meerwein, Hans et al., Chemische Berichte, vol. 90 (1957) pp. 841–852.

Primary Examiner—Natalie Trousof
Assistant Examiner—L. Hendriksen
Attorney, Agent, or Firm—John H. Shurtleff

[57] ABSTRACT

A process for the preparation of aromatic sulfohalides by reacting an aqueous solution, containing a hydrogen halide, of an aromatic diazonium halide with sulfur dioxide, wherein (a) the aqueous solution, containing the hydrogen halide, of a diazonium salt which is derived from the corresponding aromatic amine and the halogen of the desired sulfohalide is reacted with sulfur dioxide in the presence of an inert organic solvent which is immiscible or only partially miscible with water, (b) the diazonium salt is decomposed, simultaneously or subsequently, by means of a catalyst for diazonium salt decomposition and (c) the resulting reaction mixture, or the organic phase thereof after removal of the aqueous phase, is treated with an oxidizing agent.

10 Claims, No Drawings

PREPARATION OF AROMATIC SULFOHALIDES

The present invention relates to a novel process for the preparation of aromatic sulfohalides by reacting aqueous solutions of aromatic diazonium salts with sulfur dioxide.

It is known from Meerwein et al. (Chem. Ber., 90 (1957), 841 et seq.) that aromatic sulfohalides may be prepared by diazotizing the corresponding aromatic amines, reacting the diazonium salt solutions with a solution of $SO_2$ in acetic acid, and subsequently or simultaneously decomposing the diazonium salts by means of copper catalysts, especially copper halides. This may be illustrated by the synthesis of benzenesulfochloride from aniline:

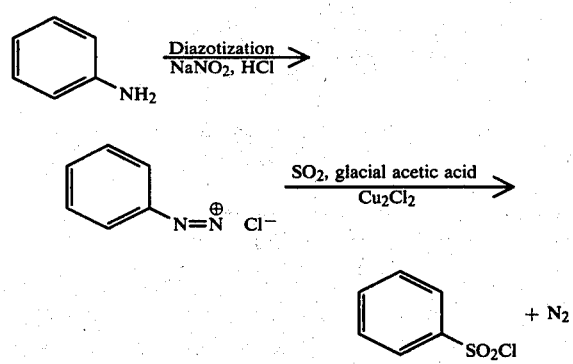

However, only in exceptional cases is the yield of sulfohalides satisfactory, and moreover the consumption of acetic acid has a substantial adverse effect on the economics of the process. By carrying out the process in the presence—as recommended by Meerwein et al.—of an organic solvent of low dielectric constant, such as benzene or carbon tetrachloride, a relative improvement in yield can be achieved in the case of p-methoxybenzenesulfochloride, but in absolute terms the yield of only about 40% still leaves much to be desired.

It is an object of the present invention to prepare the aromatic sulfohalides in higher yields, and more economically, then hitherto.

We have found that this object is achieved and that aromatic sulfohalides are obtained, in an unusual reaction sequence, by reacting an aqueous solution, containing a hydrogen halide, of an aromatic diazonium halide with sulfur dioxide if (a) the aqueous solution, containing the hydrogen halide HX, of a diazonium salt which is derived from the corresponding aromatic amine and the halogen X of the desired sulfohalide is reacted with sulfur dioxide in the presence of an inert organic solvent which is immiscible or only partially miscible with water, (b) the diazonium salt is decomposed, simultaneously or subsequently, by means of a catalyst for diazonium salt decomposition and (c) the resulting reaction mixture, or the organic phase thereof after removal of the aqueous phase, is treated with an oxidizing agent.

In principle, the diazonium salts can be derived from any diazotizable isocyclic or heterocyclic mononuclear or polynuclear primary aromatic amine. Such amines, which can carry any desired inert substituents and which preferably have the general formula $Ar(NH_2)_n$ where Ar is unsubstituted or substituted aryl and n is 1 or 2, are, for example, the monoamines and diamines of the aromatic parent compounds benzene, naphthalene, pyridine and quinoline.

Examples of suitable inert substituents are $C_1$–$C_{20}$-alkyl, $C_1$–$C_{20}$-alkoxy, $C_2$–$C_{20}$-acyl, $C_2$–$C_{20}$-acyloxy, $C_2$–$C_{20}$-carbalkoxy, carboxy, hydroxyl, mono- and di-$C_1$–$C_4$-alkylamino, halogen, eg. fluorine, chlorine and bromine, haloalkyl, hydroxyalkyl, nitro, sulfo, aryl, eg. phenyl, and aralkyl, eg. benzyl.

Accordingly, the products obtained preferably have the general formula $Ar(SO_2X)_n$ where X is halogen, preferably chlorine.

The diazotization of the amines, to be carried out before step (a), is known from innumerable examples, especially in dye chemistry, and accordingly does not require detailed discussion here. However, in order to achieve substantially complete diazotization and good success of the novel process, it has proved particularly advantageous to carry out the diazotization by means of sodium nitrite at from $-10°$ to $10°$ C. in a medium containing a hydrogen halide, using from 1.5 to 4 moles of HX and from 0.2 to 1 kg of water per mole equivalent of the amine.

In process step (a), the aqueous acidic solution, which preferably contains 10–40% by weight of the diazonium salt, is reacted with sulfur dioxide in the presence of an inert organic solvent which is immiscible, or only partially miscible, with water.

To optimize the yield of the reaction product, it is advantageous to employ not less than an equimolar amount of $SO_2$, based on diazonium salt, but in general it is advisable to use an excess of up to one mole, preferably an excess of about 0.1–0.3 mole, of $SO_2$. The amount of solvent used is—depending on its solvent power for $SO_2$ and for the sulfochloride formed—preferably 0.1–1 liter per liter of the aqueous diazonium salt solution.

In principle any solvent can be used, provided it is not significantly miscible with water, is substantially inert to aqueous acids and $SO_2$ and has adequate solvent power for $SO_2$ and for the sulfochloride formed.

Good solubility of the sulfochloride in the solvent is particularly important, so that the choice of solvent is especially determined by this consideration. On the other hand, as regards the need for low solubility in water, it suffices in principle that a separate organic phase forms. However, for technical reasons it is advantageous to use a highly water-insoluble solvent, because this facilitates the separation of the solvent from the aqueous phase, which must be carried out in the process cycle.

Examples of suitable solvents are aliphatic ethers of 4–20 carbon atoms, e.g. diethyl ether, di-n-propyl ether, diisopropyl ether, methyl ethyl ether and methyl tert.-butyl ether, aliphatic alcohols of 4–8 carbon atoms, eg. n-butanol, n-pentanol and the hexanols, aliphatic esters of 2–10 carbon atoms, eg. methyl acetate, ethyl acetate, n-propyl acetate, isopropyl acetate and the butyl acetates, aliphatic ketones of 4–10 carbon atoms, eg. methyl ethyl ketone, diethyl ketone, methyl isopropyl ketone and diisopropyl ketone, aliphatic chlorohydrocarbons of 1-4 carbon atoms, eg. methylene chloride and the dichloroethanes, trichloroethanes, dichloropropanes and trichloropropanes, those with up to two Cl atoms per carbon atom generally being preferred, aromatic hydrocarbons of 6-10 carbon atoms, eg. benzene, toluene and the xylenes, aromatic chlorohydrocarbons, eg. chlorobenzene and the dichlorobenzenes and trichlorobenzenes, nitriles, eg. benzonitrile, nitro compounds, eg. nitrobenzene, and mixtures of these solvents.

For economic and technical reasons, solvents which boil at from 50° to 150° C. under atmospheric pressure are generally preferred, since these consume least energy in the distillation steps involved in carrying out the process industrially. Amongst the groups of solvents mentioned, the ketones and aliphatic chlorohydrocarbons are particularly suitable, whilst the aromatic solvents are somewhat less suitable.

The reaction can be carried out by thoroughly mixing a solution of the solvent and sulfur dioxide with the aqueous diazonium salt solution, or thoroughly mixing the three components, namely $SO_2$, solvent and aqueous phase. In either case, the process is advantageously carried out at 10°-80° C. under atmospheric pressure or slightly superatmospheric pressure of up to about 6 bar.

In process step (b), the intermediate from step (a) is decomposed by means of a catalyst for diazonium salt decomposition, preferably at 20°-80° C., especially 30°-60° C., in the two-phase reaction mixture from step (a), the decomposition being accompanied by evolution of nitogen.

Examples of suitable decomposition catalysts are copper, tungsten and their compounds, preferably used in amounts of from 0.005 to 0.1, especially from 0.01 to 0.03, mole per mole of the amine, and employed either as a solid or, if the catalyst is water-soluble, in the form of a concentrated aqueous solution. Particularly preferred catalysts are $CuCl_2$ and $Cu_2Cl_2$.

Surprisingly, surface-active quaternary ammonium salts, used in amounts of about 0.01-0.1 mole per mole of the amine, are also suitable decomposition catalysts. Quaternary ammonium salts of the type $R-N^{\oplus}R'_3.X^{\ominus}$, where R is long-chain alkyl, the radicals R' are lower alkyl or hydroxyalkyl, eg. methyl or hydroxyethyl, and $X^{\ominus}$ is one equivalent of an anion, preferably chloride, have proved particularly suitable. Examples of such compounds are lauryltrimethylammonium chloride and stearyltrimethylammonium chloride.

The surface activity of the quaternary ammonium salts does not have to be particularly pronounced. Rather, it suffices if the salts are adequately organophilic. Examples of such salts are the tetrabutylammonium salts and trimethylbenzylammonium salts.

If a copper salt is used as the decomposition catalyst, surface-active compounds quite generally accelerate the decomposition and accordingly increase the space-time yield. The amount of surfactant, which can be anionic, non-ionic or cationic, is preferably from 0.01 to 0.1 mole per mole of the amine employed. In the case of such use conjointly with copper salts, it is once again advantageous to employ cationic surface-active quaternary ammonium salts, since they themselves also act as decomposition catalysts and have the particular advantage that the amount of copper salt required can be as little as one-tenth of the amount needed to achieve the same effect with copper salt alone.

The nitrogen liberated carries with it some of the sulfur dioxide, which can be removed from the exit gas stream in a conventional manner, for example by solvent washing, and be recycled to process step (b). The proportion of recoverable $SO_2$ can be increased by expelling any excess from the reaction mixture by heating after completion of the reaction, ie. when no more nitrogen is evolved.

In an alternative embodiment, the reaction can be carried out simultaneously with $SO_2$ and with the catalyst. This method is as a rule preferable, since it permits an increase in space-time yield and since the shorter overall reaction time results in less formation of by-products.

The product obtained from step (b) is an aqueous organic mixture, of which the organic phase contains the sulfochloride.

In process step (c), this mixture is treated with an oxidizing agent at 0°-100° C., preferably 20°-50° C., under atmospheric pressure or slightly superatmospheric pressure, namely up to about 6 bar. This oxidizing treatment is based on the observation that as a rule sulfinic acids are formed as by-products in step (b), in amounts of from about 5 to 30 mole %, based on amine, the amount formed depending on the nature of this amine. Surprisingly, the sulfinic acids can readily be oxidized to the sulfochloride, so that the yield of the latter can be increased substantially. In principle, any oxidizing agent can be used, but for technical reasons hydrogen peroxide and free halogen, especially chlorine gas, are preferred. The amount of oxidizing agent required is about 0.05-0.5 mole, as a rule 0.2-0.3 mole, per mole of diazonium salt employed. The sulfinic acids can be detected by high pressure liquid chromatography (HPLC). As a rule, the oxidation is complete after about 5-30 minutes.

Next, the aqueous phase is separated from the organic phase. After processing in a conventional manner to recover the decomposition catalyst, the aqueous phase is discarded.

The aqueous phase can also be separated off before the oxidative treatment, but as a rule it is advisable to carry out this step after the oxidation, since the aqueous phase takes up the water-soluble by-products, inter alia salts and some of the sulfinic acid.

Following this process step, the reaction mixture is worked up in a conventional manner to obtain the sulfohalide. Frequently, the organic phase containing the sulfohalide can also be used direct for further syntheses requiring the sulfohalide.

The aromatic sulfohalides are generally employed as intermediates in organic syntheses. For example, plant growth regulators and herbicides of the arylsulfonylurea type are prepared by first converting an aromatic sulfohalide to the sulfamide, reacting the latter with phosgene to form the sulfoisocyanate and then converting this to the urea derivative by adduct formation with an amine (cf., for example, U.S. Pat. No. 4,169,719). The economics of preparation of such products are in general substantially improved by employing the process according to the invention.

EXAMPLE 1

Preparation of 2-chlorobenzenesulfochloride

To 100 g of cooled 36% strength by weight hydrochloric acid (=1 mole of HCl) were added first 32 g (about 0.25 mole) of 2-chloroaniline and then, in the course of 15 min at 0°-5° C., 76 g of a 25% strength by weight sodium nitrite solution (=0.28 mole of $NaNO_2$). Thereafter, the diazonium salt solution obtained was stirred for 10 min at 0° C., following which the excess nitrous acid was destroyed with a small amount of urea.

The diazonium salt solution was then brought into contact with a solution of 100 ml of 1,2-dichloroethane and 21 g (0.33 mole) of $SO_2$ at 20° C., using vigorous stirring. Thereafter, a concentrated aqueous solution of 0.625 g (3.7 millimoles) of copper-II chloride dihydrate was added to the mixture, and the batch was heated to 50° C., with stirring, and kept at this temperature until no more nitrogen was liberated; this required 80 min.

Thereafter, 2.5 g (35 millimoles) of chlorine gas were passed into the mixture at 50° C. After 5 minutes, the phases were separated and the organic phase was worked up in a conventional manner to give the required product. The yield of pure 2-chlorobenzenesulfochloride (boiling point 144°–146° C./21 mbar) was about 93%.

EXAMPLE 2

Preparation of 4-methoxybenzenesulfochloride

A diazonium salt solution, prepared similarly to Example 1 from p-anisidine, was brought into intimate contact with a solution of 100 ml of diethyl ketone and 21 g (0.33 mole) of $SO_2$, and was then decomposed using 0.5 g of $CuCl_2.2H_2O$ and 1 g of tetrabutylammonium chloride at 40° C. Further treatment with 4.5 g (63 millimoles) of $Cl_2$ and subsequent conventional working up of the reaction mixture gave 4-methoxybenzenesulfochloride in 87% yield; melting point 43° C.

EXAMPLE 3

Preparation of 2-methoxybenzenesulfochloride

A diazonium salt solution, prepared similarly to Example 1 from o-anisidine, was brought into intimate contact, at 0° C., with a solution of 100 ml of 1,2-dichloroethane and 21 g (0.33 mole) of $SO_2$, and was then decomposed using 0.5 g of $CuCl_2$ and 1 g of dodecyldimethylbenzylammonium chloride at 40° C. 4.3 g of a 30% strength by weight aqueous hydrogen peroxide solution (=38 millimoles of $H_2O_2$) were then added to the mixture, and after a reaction time of 3 minutes the batch was worked up in a conventional manner. The yield of 2-methoxybenzenesulfochloride was 80%; boiling point 134°–138° C./0.7 mbar.

EXAMPLE 4

Preparation of 4-methylbenzenesulfochloride (tosyl chloride)

This compound was prepared in 74% yield from p-toluidine by a method similar to Example 2; melting point 67°–68° C. (from naphtha).

We claim:

1. A process for the preparation of an aromatic sulfohalide by reacting an aqueous solution, containing a hydrogen halide, of an aromatic diazonium halide with sulfur dioxide, which process comprises:
   (a) reacting
      (1) an aqueous solution which does not dissolve sulfur dioxide, said solution essentially containing the hydrogen halide HX of a diazonium salt which is derived from the corresponding aromatic amine and the halogen X of the desired sulfohalide, with
      (2) sulfur dioxide in the presence of an inert organic solvent which dissolves the sulfur dioxide but which is immiscible or only partially miscible with water;
   (b) decomposing the diazonium salt, simultaneously or subsequently, by means of a catalyst for diazonium salt decomposition; and
   (c) treating the resulting reaction mixture, or the organic phase thereof after removal of the aqueous phase, with an oxidizing agent.

2. A process as claimed in claim 1, wherein the organic solvent used is an aliphatic ketone of 4–10 carbon atoms.

3. A process as claimed in claim 1, wherein the organic solvent used is an aliphatic chlorohydrocarbon of 1–4 carbon atoms, which contains one or two Cl atoms per carbon atom.

4. A process as claimed in claim 1, wherein $CuCl_2$ or $Cu_2Cl_2$ is used as the catalyst for diazonium salt decomposition.

5. A process as claimed in claim 4, wherein a surfactant is used additionally to the copper salt for decomposing the diazonium salt.

6. A process as claimed in claim 5, wherein a surface-active quaternary ammonium salt is used as the surfactant.

7. A process as claimed in claim 1, wherein a surface-active quaternary ammonium salt is used as the catalyst for diazonium salt decomposition.

8. A process as claimed in claim 1, wherein chlorine gas is used as the oxidizing agent.

9. A process as claimed in claim 1, wherein hydrogen peroxide is used as the oxidizing agent.

10. A process as claimed in claim 1 wherein the aromatic amine has the formula $Ar(NH_2)_n$ where Ar is unsubstituted aryl or aryl bearing inert substituents, said aryl being selected from the group consisting of benzene, naphthalene, pyridine and quinoline, and n is 1 or 2, and where the corresponding sulfohalide product has the formula $Ar(SO_2X)_n$ wherein Ar and n have the same meaning given above and X is halogen.

* * * * *